(12) United States Patent
Mueller

(10) Patent No.: US 8,329,107 B2
(45) Date of Patent: Dec. 11, 2012

(54) SENSOR THAT COMPENSATES FOR DETERIORATION OF A LUMINESCABLE MEDIUM

(75) Inventor: Cord Mueller, Middletown, CT (US)

(73) Assignee: Ric Investments, LLC, Wilmington, DE (US)

( * ) Notice: Subject to any disclaimer, the term of this patent is extended or adjusted under 35 U.S.C. 154(b) by 0 days.

(21) Appl. No.: 13/205,178

(22) Filed: Aug. 8, 2011

(65) Prior Publication Data

US 2011/0293480 A1    Dec. 1, 2011

Related U.S. Application Data

(62) Division of application No. 11/866,046, filed on Oct. 2, 2007, now Pat. No. 8,021,615.

(51) Int. Cl.
G01N 21/64    (2006.01)
G01N 21/76    (2006.01)
G01N 21/00    (2006.01)
G01M 15/00    (2006.01)
G01J 3/30     (2006.01)
G01N 21/75    (2006.01)

(52) U.S. Cl. .......... 422/83; 422/82.08; 422/82.09; 73/1.06; 73/114.73; 436/164; 436/172; 356/311; 356/432; 356/437

(58) Field of Classification Search .......... None
See application file for complete search history.

(56) References Cited

U.S. PATENT DOCUMENTS

| | | | |
|---|---|---|---|
| 6,325,978 B1 | 12/2001 | Labuda | |
| 6,616,896 B2 | 9/2003 | Labuda et al. | |
| 6,632,402 B2 | 10/2003 | Blazewicz | |
| 6,815,211 B1 | 11/2004 | Blazewicz | |
| 6,905,881 B2 | 6/2005 | Sammak | |
| 6,927,851 B2 * | 8/2005 | McCaffrey et al. | 356/311 |
| 7,040,139 B2 * | 5/2006 | Sunshine | 73/23.2 |
| 2004/0013570 A1 * | 1/2004 | Labuda et al. | 422/82.08 |
| 2004/0161370 A1 | 8/2004 | Sunshine | |
| 2006/0042350 A1 * | 3/2006 | Tice | 73/1.06 |

* cited by examiner

Primary Examiner — In Suk Bullock
Assistant Examiner — Jennifer Wecker

(57) ABSTRACT

A sensor that generates an output signal in response to a stimulus, where the output signal is generated with a predetermined relationship to one or more properties of the stimulus such that the one or more properties of the stimulus can be determined as a function of the output signal. In one embodiment, the sensor includes a component, a sensor processor, and a transmitter. The component deteriorates, thereby causing predictable fluctuations in the predetermined relationship between the output signal and the one or more properties of the stimulus. The sensor processor provides information related to the deterioration of the component. The transmitter wirelessly transmits the information provided by the processor.

9 Claims, 4 Drawing Sheets

SENSOR THAT COMPENSATES FOR DETERIORATION OF A LUMINESCABLE MEDIUM

CROSS-REFERENCE TO RELATED APPLICATIONS

This application claims priority under 35 U.S.C. §119(e) from provisional U.S. patent application Ser. No. 60/849,951 filed Oct. 6, 2006 the contents of which are incorporated herein by reference.

BACKGROUND OF THE INVENTION

1. Field of the Invention

The present invention relates to a system and method of compensating for the deterioration of a luminescable medium in a sensor that determines information related to one or more analytes in a body of gas.

2. Description of the Related Art

Sensors including a luminescable medium that measure one or more aspects of the luminescence of the luminescable medium in order to determine information related to an analyte in a body of gas in contact with the luminescable medium are known. U.S. Pat. Nos. 6,325,978; 6,632,402; 6,616,896 and 6,815,211, the contents of each of which are incorporated herein by reference, all disclose an example of such a sensor that uses luminescence quenching to determine the concentration of a gas, such as oxygen, in the gas flowing through a sample cell.

Typically, over time, the accuracy of these luminescence based sensors is degraded by deterioration of the luminescable medium due to photo-bleaching, radical formation, and/or other phenomena. Without relatively frequent calibration and/or relatively frequent replacement of the luminescable medium, conventional sensors of this type may be unreliable due to this degradation. Other drawbacks associated with the deterioration of the luminescable medium also exist.

SUMMARY OF THE INVENTION

One aspect of the invention relates to a sensor configured to determine information related to one or more gaseous analytes in a body of gas. In one embodiment, the sensor comprises a first sensor section and a second sensor section. The first sensor section comprises an emitter, the emitter configured to emit electromagnetic radiation. The second sensor section is configured to removably couple to the first sensor section and comprises a luminescable medium, a storage module, and a transmitter. The luminescable medium is in operative communication with the body of gas and is arranged to receive electromagnetic radiation from the emitter if the second sensor section is removably coupled to the first sensor section. The luminescable medium emits luminescent radiation in response to the electromagnetic radiation it receives from the emitter such that information related to the one or more gaseous analytes in the body of gas can be determined as a function of one or more properties of the luminescent radiation. The storage module stores information related to a deterioration of the luminescable medium, wherein the deterioration of the luminescable medium impacts the emission of the luminescent radiation by the luminescable medium. The transmitter transmits the information related to the deterioration of the luminescable medium.

Another aspect of the invention relates to a system configured to determine information related to one or more gaseous analytes in a body of gas. In one embodiment, the system comprises a processor and a sensor. The sensor comprises a first sensor section and a second sensor section. The first sensor section comprises an emitter and a photosensitive detector. The emitter is configured to emit amplitude modulated electromagnetic radiation. The photosensitive detector is configured to receive electromagnetic radiation and generate one or more output signals in response to the received electromagnetic radiation, the output signals indicating an amplitude of the received electromagnetic radiation. The second sensor section is configured to removably couple to the first sensor section and comprises a luminescable medium, a storage module, and a transmitter.

The luminescable medium is in operative communication with the body of gas and arranged to receive the amplitude modulated electromagnetic radiation from the emitter if the second sensor section is removably coupled to the first sensor section. The luminescable medium emits luminescent radiation in response to the electromagnetic radiation it receives from the emitter such that information related to the one or more gaseous analytes in the body of gas can be determined as a function of one or more properties of the luminescent radiation. The luminescable medium is further arranged such that a portion of the luminescent radiation is directed to the photosensitive detector if the second sensor section is removably coupled to the first sensor section. The storage module stores information related to a deterioration of the luminescable medium, wherein the deterioration of the luminescable medium impacts the emission of the luminescent radiation by the luminescable medium.

The transmitter transmits the information related to the deterioration of the luminescable medium. The processor (i) receives the output signal generated by the photosensitive detector, (ii) receives the information related to the deterioration of the luminescable medium that is wirelessly transmitted by the transmitter, and (iii) determines the information related to the one or more gaseous analytes based on the output signal generated by the photosensitive detector and the information received from the transmitter.

Yet another aspect of the invention relates to a sensor that generates an output signal in response to a stimulus, wherein the output signal is generated with a predetermined relationship to one or more properties of the stimulus such that the one or more properties of the stimulus can be determined as a function of the output signal. In one embodiment the sensor comprises a component, a sensor processor, and a transmitter. The component deteriorates, thereby causing predictable fluctuations in the predetermined relationship between the output signal and the one or more properties of the stimulus. The sensor processor provides information related to the deterioration of the component. The transmitter wirelessly transmits the information provided by the processor.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1A:
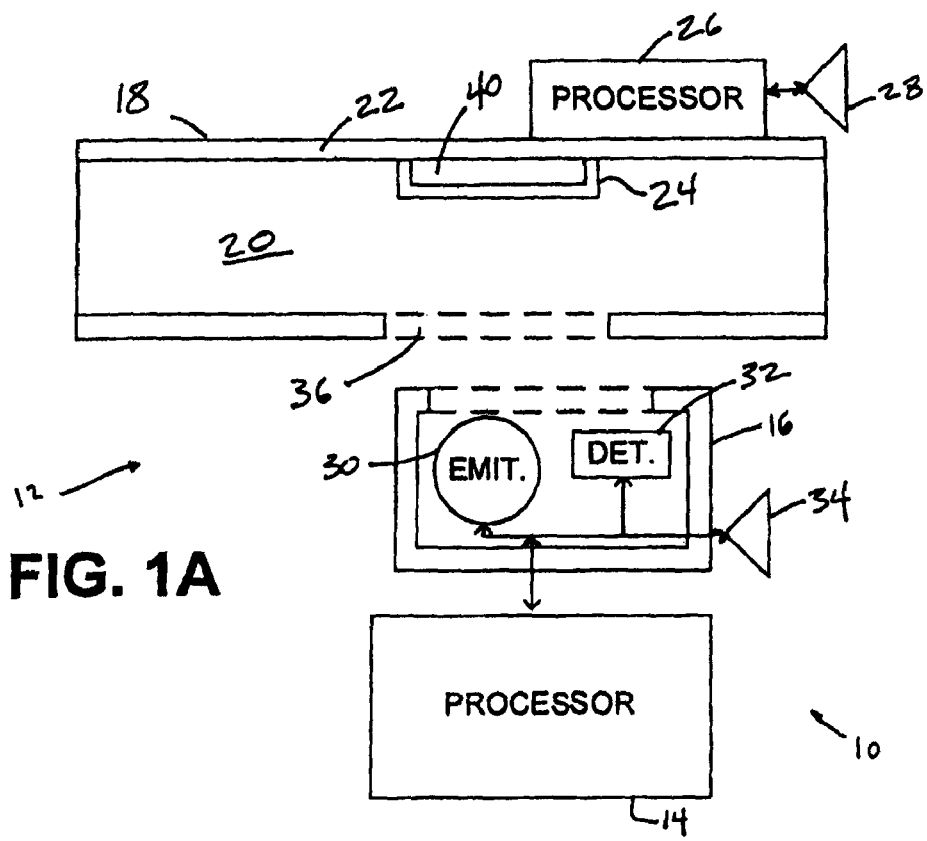
FIG. 1A illustrates a system configured to determine information related to one or more analytes in a body of gas, according to one embodiment of the invention.

Turning to FIG. 1A, a system 10 configured to determine information related to one or more analytes or constituents in a body gas is illustrated. System 10 includes a sensor 12 and a processor 14. Sensor 12 includes a first sensor section 16 and a second sensor section 18. First sensor section 16 and second sensor section 18 can, in one embodiment, be removably coupled to each other. FIG. 1A illustrates first sensor section 16 uncoupled from second sensor section 18.

Figure 1B:
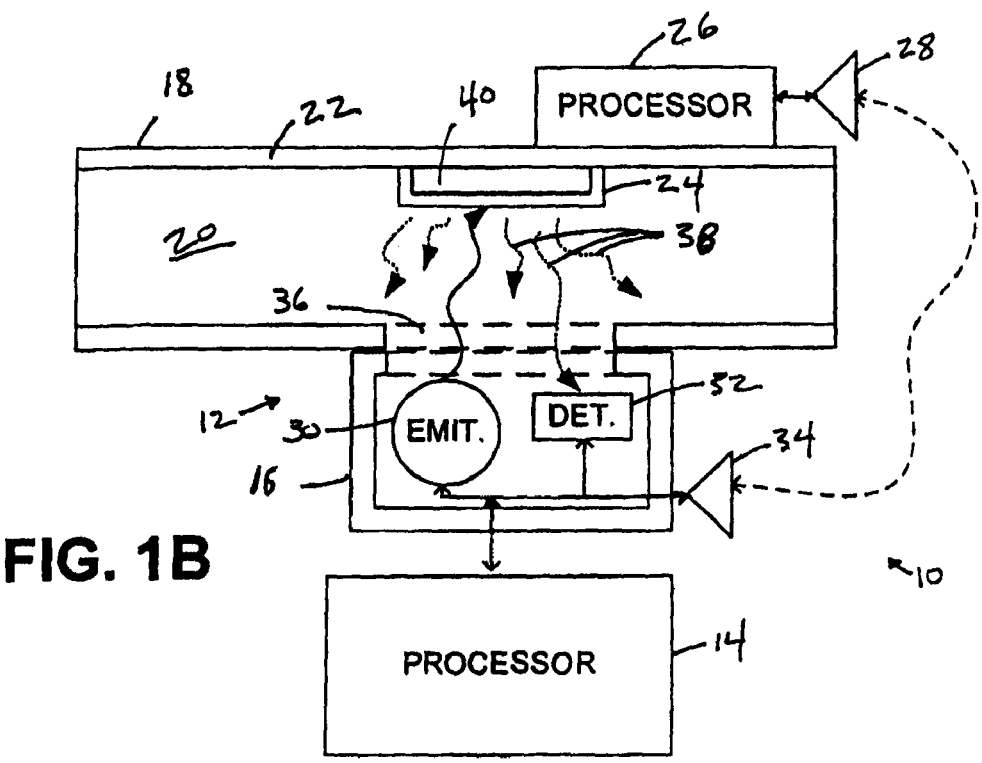
FIG. 1B illustrates a system configured to determine information related to one or more analytes in a body of gas, according to one embodiment of the invention.

FIG. 1B schematically illustrates system 10 when first sensor section 16 and second sensor section 18 are coupled together. Second sensor section 18 provides a flow path 20 formed by a conduit 22 through which gas may pass. If first sensor section 16 is coupled to second sensor section 18 (e.g., as illustrated in FIG. 1B), first sensor section 16 is operable to generate an output signal that is provided to processor 14 via an operative communication link (e.g., a wired link, a wireless link, a discrete link, a link via a network, etc.) therebetween. Based on the output signal generated by first sensor section 16, processor 14 determines information related to one or more properties of one or more analytes or constituents included in the gas disposed within flow path 20. An example of an analyte or constituent in a flow of gas that is monitored via the luminescence-based technique is oxygen.

In one embodiment, conduit 22 is adapted to carry gas to and/or from a patient. Thus, conduit 22 may be coupled with another conduit, circuit, or tubing that delivers gas to conduit 22. In a more particular example, conduit 22 may receive gas from a patient interface appliance configured to communicate with an airway of the patient. Some examples of the patient interface appliance may include, for example, an endotracheal tube, a nasal cannula, a tracheotomy tube, a mask, or other patient interface appliances. The present invention is not limited to these examples, and contemplates determination of analytes in any body of gas.

As can be seen in FIGS. 1A and 1B, in one embodiment, second sensor section 18 includes a luminescable medium 24, a processor 26, and a transmitter/receiver 28. In one embodiment, first sensor section 16 includes an emitter 30, a photosensitive detector 32, and a transmitter receiver 34.

It should be appreciated that a variety of mechanisms may be implemented to removably couple sensor sections 16 and 18. In some embodiments a seating area is provided on an outer surface of conduit 22 that is adapted to securely receive a housing that houses first sensor section 16. For example, sensor sections 16 and 18 may be coupled in the manner described in U.S. Pat. No. 6,616,896 to Labuda et al., entitled "OXYGEN MONITORING APPARATUS," and issued Sep. 9, 2003 (hereafter "the '896 patent"), or in the manner described in U.S. Pat. No. 6,632,402 to Blazewicz et al., entitled "OXYGEN MONITORING APPARATUS," and issued Oct. 14, 2003 (hereafter "the '402 patent"). Further, both of these references describe sensors that (1) include components similar to some or all of emitter 30, photosensitive detector 32, and/or luminescable medium 24, and (2) determine information related to one or more analytes in a body of gas in a manner similar to sensor 12. Both the '402 patent and the '896 patent are hereby incorporated, in their entireties, into this disclosure by reference. These examples are not intended to be limiting, and it should be appreciated that any suitable method for coupling sensor sections 16 and 18 can be used. In addition, in another embodiment sensor sections 16 and 18 are permanently connected to one another, or at least not readily uncoupled.

When sensor sections 16 and 18 are coupled, emitter 30 emits electromagnetic radiation that is directed onto luminescable medium 24. As will be discussed further below, the electromagnetic radiation emitted by emitter 30 includes electromagnetic radiation with a wavelength that causes luminescable medium 24 to luminensce. Emitter 30 may include one or more Organic Light Emitting Diodes ("OLEDs"), lasers (e.g., diode lasers or other laser sources), Light Emitting Diodes ("LEDs"), Hot Cathode Fluorescent Lamps ("HCFLs"), Cold Cathode Fluorescent Lamps ("CCFLs"), incandescent lamps, halogen bulbs, received ambient light, and/or other electromagnetic radiation sources.

In one implementation, emitter 30 includes one or more green and/or blue LEDs. These LEDs typically have high intensity in the luminescable composition absorption region of luminescable medium 24 and output smaller amounts of radiation at other wavelengths (e.g., red and/or infrared). This minimizes stray interfering light and photodegradation of sensor 12.

While, the present invention is by no means limited to the use of LEDs, other advantages of implementing LEDs as emitter 30 include their light weight, compactness, low power consumption, low voltage requirements, low heat production, reliability, ruggedness, relatively low cost, and stability. Also they can be switched on and off very quickly, reliably, and reproducibly.

In some implementations, system 10 may include one or more optical elements (not shown) disposed within one or both of first sensor section 16 and second sensor section 18 to guide, focus, and/or otherwise process radiation emitted by emitter 30. For example, one or more lenses may collimate the radiation in a selected direction. As more particular examples, both of the incorporated '896 and '402 patents disclose the use of optical elements that process radiation emitted by an emitter similar to emitter 30.

When sensor sections 16 and 18 are coupled, the electromagnetic radiation from emitter 30 may arrive at luminescable medium 24 with a predetermined amplitude modulation (e.g., having a predetermined frequency, having a predetermined maximum and/or minimum amplitude, etc.). In one embodiment, emitter 30 may be driven to emit the electromagnetic radiation with the predetermined amplitude modulation. In another embodiment, first sensor section 16 may include one or more optical elements (not shown) that modulate the amplitude of electromagnetic radiation emitted by emitter 30. The one or more optical elements may include one or more periodically driven active elements (e.g., a liquid crystal stack, etc.) and/or one or more passive elements that are periodically moved into and out of an optical path of the electromagnetic radiation emitted by emitter 30 (e.g., filters, half-mirrors, etc.).

Second sensor section 18 may include a window 36 formed in a wall of conduit 22. Window 36 may be substantially transparent to enable electromagnetic radiation, such as the electromagnetic radiation emitted by emitter 30, to enter and/or exit the interior of conduit 22 when sensor sections 16 and 18 are coupled. For instance, window 36 may be formed of sapphire, one or more polymers (e.g., polyethelyne, etc.), a glass, and/or other substantially transparent materials. In some embodiments (not shown), conduit 22 may include two windows similar to window 36. As is shown and described in the '402 patent, the two windows may be disposed in conduit 22 opposite from each other to enable electromagnetic radiation to pass through conduit 22. In this embodiment, photosensitive detector 32 may be positioned on an opposite side of conduit 22 from emitter 30 when sensor sections 16 and 18 are coupled.

Luminescable medium 24 is a medium that, in response to radiation from emitter 30 and/or some other excitation energy, luminescence to emit electromagnetic radiation, indicated by wavy lines 38, in a substantially omni-directional manner at a wavelength different from that of the electromagnetic radiation provided by emitter 30. The intensity and/or persistence of this luminesced electromagnetic radiation 38 rises and falls according to the relative amounts of one or more analytes included in the body of gas within conduit 22. In one embodiment, oxygen causes a modification of the intensity and/or persistence of luminescent radiation 38 by quenching the luminescence reaction. As the concentration of oxygen increases, the modification of the intensity and/or persistence of luminescent radiation 38 will decrease. In one embodiment, luminescable medium 24 is formed as a luminescent film. For example, both of the incorporated '896 and '402 patents disclose films that may be employed as luminescable medium 24.

In the embodiment illustrated in FIGS. 1A and 1B, luminescable medium 24 is disposed in contact with, in close proximity with, or otherwise thermally coupled to a thermal capacitor 40. Thermal capacitor 40 is employed to maintain luminescable medium 24 at a substantially constant operating temperature and thereby reduce or eliminate inaccuracies in system 10 attributable to variations in the temperature of luminescable medium 24. Thus, thermal capacitor 40 is any device that accomplishes this function, such as a heater controlled in a feedback fashion based on an output of a temperature sensor, a heat sink, or the like.

Photosensitive detector 32 is positioned within first sensor section 16 such that if sensor sections 16 and 18 are coupled, photosensitive detector 32 receives at least a portion of luminesced electromagnetic radiation 38 from luminescable medium 24. Based on the received radiation, photosensitive detector 32 generates one or more output signals related to one or more properties of the received radiation. For example, the one or more output signals may be related to an amount of the radiation, an intensity of the radiation, a modulation of the radiation, and/or other properties of the radiation. In one embodiment, photosensitive detector 32 includes a PIN diode. In other embodiments, other photosensitive devices are employed as photosensitive detector 32. For instance, photosensitive detector 32 may take the form of a diode array, a CCD chip, a CMOS chip, a photo-multiplier tube and/or other photosensitive devices.

Figure 2:
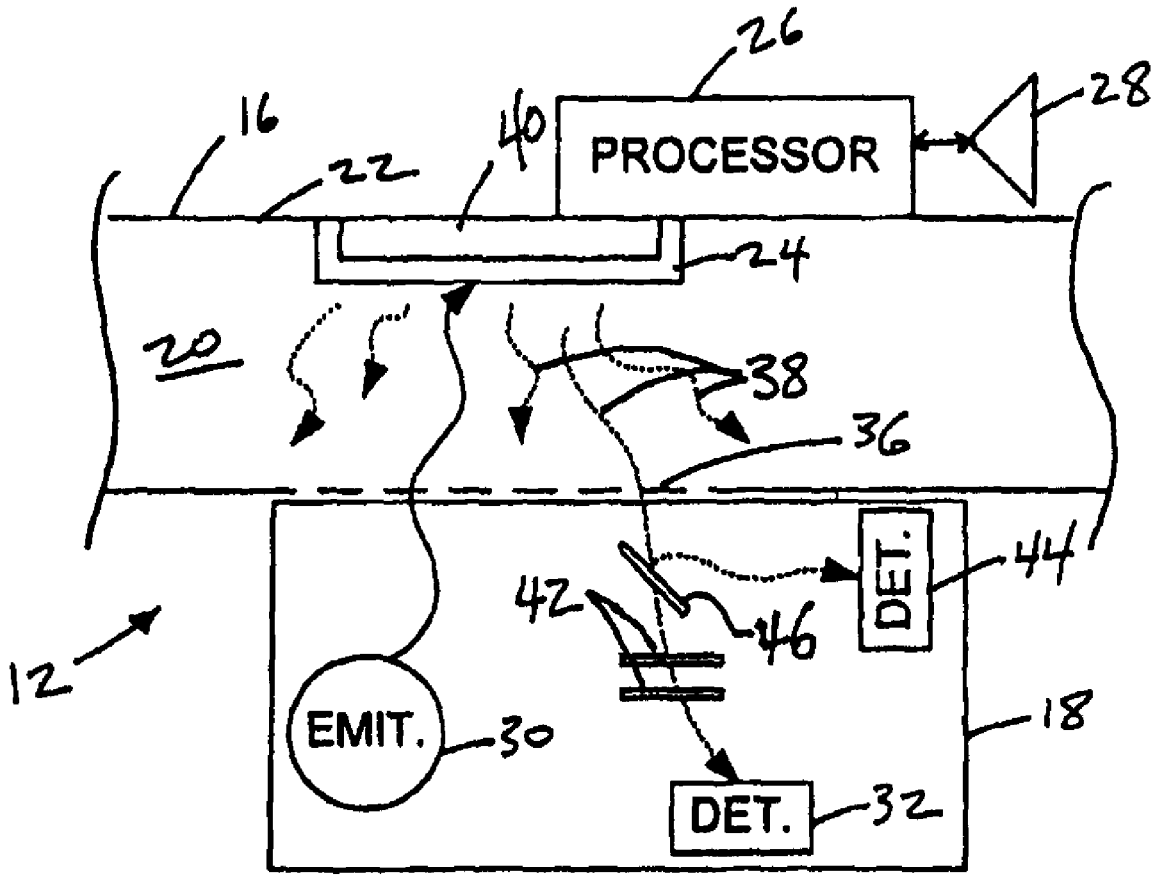
FIG. 2 illustrates a configuration of a sensor configured to determine information related to one or more analytes in a body of gas, according to one embodiment of the invention.

FIG. 2 illustrates an embodiment of sensor 12 including photosensitive detector 32 in which one or more filter elements 42 are positioned within first sensor section 16 between luminescable medium 24 and photosensitive detector 32. As is described in both the incorporated '896 and '402 patents, filter elements 42 are typically designed to prevent electromagnetic radiation that is not emitted by luminescable medium 24 from becoming incident on photosensitive detector 32. For instance, in one embodiment, filter elements 42 are wavelength specific and permit luminescence radiation 38 to pass therethrough to become incident on photosensitive detector 32 while substantially blocking radiation with other wavelengths.

In the embodiment of sensor 12 illustrated in FIG. 2, first sensor section 16 also includes a reference photosensitive detector 44 and a beam splitting element 46. As is described in the incorporated '896 patent, beam splitting element 46 may direct a portion of the radiation propagating toward photosensitive detector 32 onto reference photosensitive detector 44. One or more output signals generated by reference photosensitive detector 44 may be used as a reference to account, and compensate, for system noise (e.g., intensity fluctuations in emitter 30, etc.) in the one or more output signals generated by photosensitive detector 32.

It should be appreciated that although filters 42, reference photosensitive detector 44, and beam splitting element 46 are shown in FIG. 2 as being disposed in first sensor section 16, this is for illustrative purposes. In other embodiments, some or all of beam splitting element 46, reference photosensitive detector 44, and/or one or more of filters 42 may be disposed within first sensor section 16.

Figure 3:
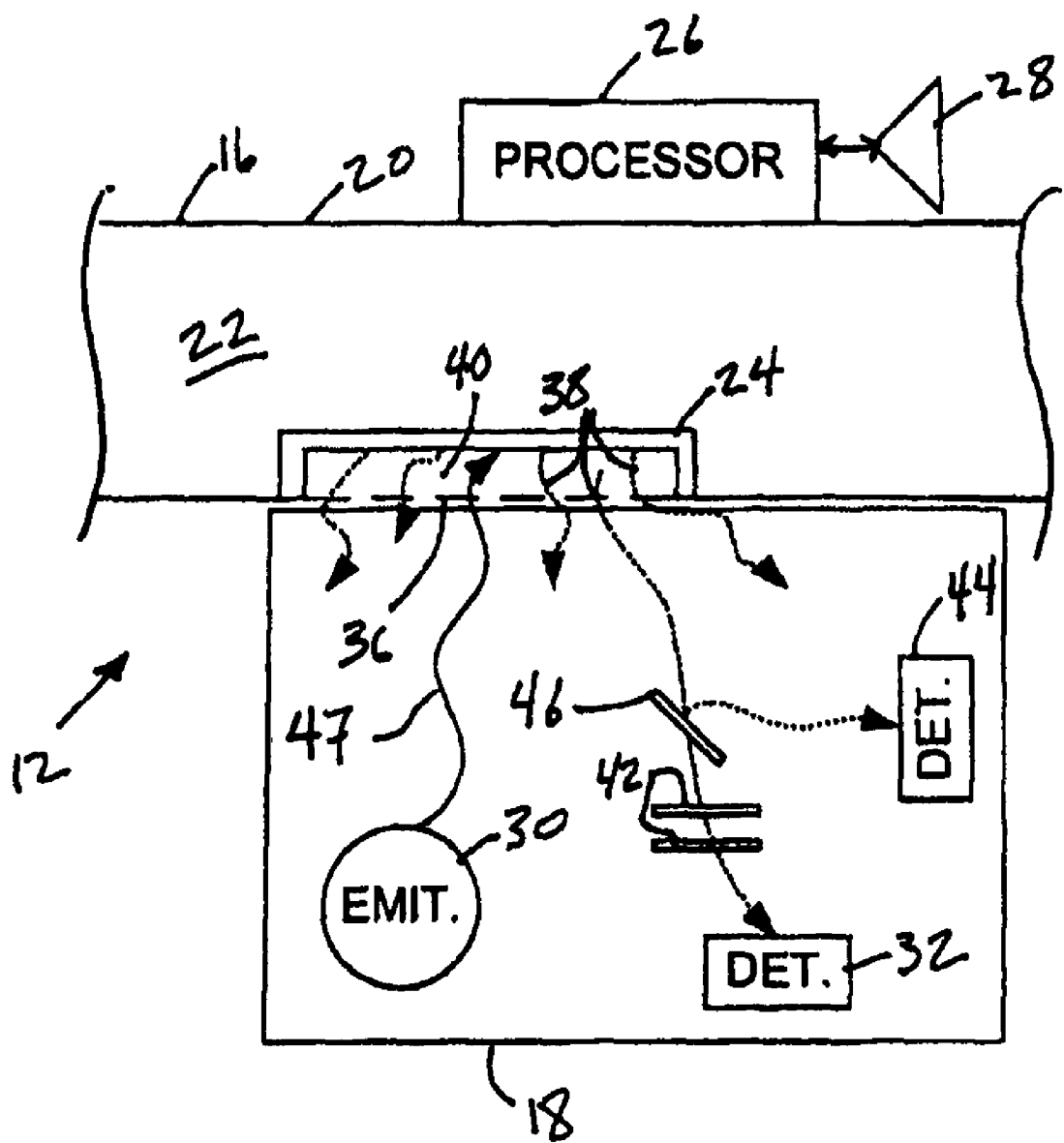
FIG. 3 illustrates a configuration of a sensor configured to determine information related to one or more analytes in a body of gas, according to one embodiment of the invention.

FIG. 3 illustrates yet another configuration of sensor 12. In the configuration illustrated in FIG. 3, thermal capacitor 40 is at least partially transparent, and is located adjacent to window 36. In this configuration luminescable medium 24 is positioned in thermal communication with thermal capacitor 40 on an opposite side of capacitor 40 from window 36. Luminescable medium 24 is exposed to flow path 20 on a side of luminescable medium 24 that is opposite the boundary between capacitor 40 and luminescable medium 24. As can be seen, electromagnetic radiation 47 emitted by emitter 30 passes through both window 36 and thermal capacitor 40 to become incident luminescable medium 24. Luminescent radiation 38 emitted from luminescable medium 24 proceeds back through thermal capacitor 40 and window 36 to become incident on one or both of photosensitive detectors 32 and/or 44, in substantially the same manner as is described above.

Returning to FIGS. 1A and 1B, transmitter/receivers 28 and 34 transmit signals from and/or receive signals to each other. More particularly, in one embodiment, transmitter/receivers 28 and 34 transmit and/or receive signals wirelessly. This may be beneficial in instances in which system 10 is deployed in a medical setting, as exposed communications lines and/or leads may be discouraged or prohibited. However, in other embodiments, transmitter/receivers 38 and 34 may transmit and/or receive signals via a wired connection. These embodiments may include instances in which system 10 is deployed in a medical setting. As can be see in FIGS. 1A and 1B, transmitter/receiver 28 interfaces with processor 26 to transmit signals from processor 26 and/or receive signals for processor 26. Transmitter/receiver 34 interfaces with processor 14 to transmit signals from processor 14 and/or receive signals for processor 14.

In some embodiments, luminescable medium 24 may deteriorate over time, causing fluctuations in the response (e.g., the intensity and/or the persistence of luminescent radiation 38) of luminescable medium 24 to an excitement energy (e.g., electromagnetic radiation from emitter 30). In other words, chemical and/or physical changes that occur within luminescable medium 24 due to one or both of use and age may cause luminescable medium 24 to react differently to the same excitement energy applied thereto at two non-adjacent points in time. As the deterioration of luminescable medium 24 continues, it may impact the accuracy of sensor 10 in monitoring its intended stimulus (the one or more analytes or constituents in the body of gas) by changing the correlation between the output signal representative of one or more properties of luminescence radiation 38 luminesced by luminescable medium 24 and the stimulus. Some examples of phenomena that may cause the deterioration of luminescable medium 24 include photo-bleaching, the formation of oxygen radicals, and/or other phenomena.

Processor 26 determines information related to the deterioration of luminescable medium 24 that increases with age and/or use of luminescable medium 24. This information is then transmitted from processor 26 by transmitter/receiver 28, and is received by processor 14 via transmitter/receiver 34. As is discussed further below, processor 14 also receives the output signals of photosensitive detector 32. Processor 14 then determines information related to one or more analytes in the body of gas present in flow path 22 based on the output signals and the information received from processor 26.

Figure 4:
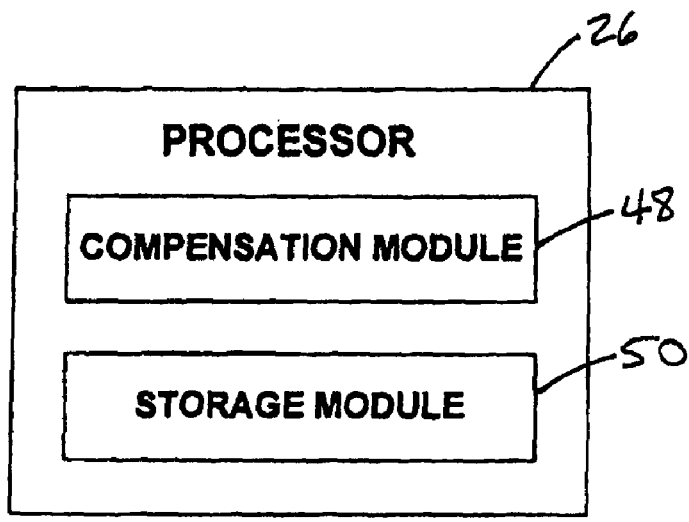
FIG. 4 illustrates a processor disposed within a sensor configured to determine information related to one or more analytes in a body of gas, according to one embodiment of the invention.

FIG. 4 illustrates processor 26, according to one or more embodiments of the invention. As is shown, in one embodiment, processor 26 includes a compensation module 48 and a storage module 50. Modules 48 and 50 may be implemented in software, hardware, firmware, some combination of software, hardware, and/or firmware; and/or otherwise implemented. It should be appreciated that although modules 48 and 50 are illustrated in FIG. 4 as being co-located within a single processing unit, processor 26 may include multiple processing units, and that some of these processing units may be located remotely from each other within second sensor section 18. In such embodiments, modules 48 and 50 may be located remotely from the other modules and operative communication between the modules may be achieved via one or more communication links. Such communication links may be wireless or hard wired.

Compensation module 48 determines the information related to the deterioration of luminescable medium 24. As was mentioned previously, the deterioration of luminescable medium 24 tends to progress with age and/or use. Therefore, in one embodiment, compensation module 48 monitors the amount of time (1) that luminescable medium 24 has been installed sensor 12 ("$t_{age}$"), and/or (2) that luminescable medium 24 has been receiving electromagnetic radiation from emitter 30 in sensor 12 ("$t_{use}$"). It should be apparent that in some embodiments one or both of $t_{age}$ and $t_{use}$ may or may not be reset when sensor 10 is calibrated in a manner that accounts for the deterioration of luminescable medium 24.

To monitor $t_{age}$ and $t_{use}$, compensation module 48 may include a clock, a timer, and/or some other timekeeping component. The determination of $t_{age}$ is fairly straight forward, as it simply requires a continuously running time period. Determining $t_{use}$ requires that compensation module 48 be informed of when luminescable medium 24 is receiving electromagnetic radiation from emitter 30 (or some approximation of this time period).

For example, in one embodiment, compensation module 48 is in communication with a photosensitive detector, illustrated in FIG. 2 as photosensitive detector 32, disposed in second sensor section 18 at or near luminescable medium 24. Photosensitive detector 32 is adapted to detect radiation emitted by emitter 30, and compensation module 48 counts the time during which photosensitive detector 32 detects radiation emitted by emitter 30 toward $t_{use}$.

Returning to FIG. 4, in another embodiment, processor 26 receives signals via transmitter/receiver 28 indicating commencement/abatement of electromagnetic radiation being directed from emitter 30 to luminescable medium 24. In some embodiments, $t_{use}$ may be merely an approximation of the time that luminescable medium 24 is in use. For example, second sensor section 18 (and/or first sensor section 16) may include a detector (not shown) that detects when sensor sections 16 and 18 are coupled, and compensation module 48 may measure the time that sensor sections 16 and 18 are coupled as $t_{use}$.

In one embodiment, compensation module 48 executes an algorithm that determines a compensation factor as a function of one or both of $t_{age}$ and $t_{use}$. The compensation factor is then transmitted to processor 14 via transmitter/receivers 28 and 34 to be implemented by processor 14 in the determination of information related to the one or more analytes present in the body of gas. The algorithm may include a mathematical function, a look-up table, and/or other forms of algorithms. In another embodiment, compensation module 48 causes $t_{age}$ and/or $t_{use}$ to be transmitted to processor 14 via transmitter/receivers 28 and 34, and processor 14 implements $t_{age}$ and/or $t_{use}$ to determine the compensation factor.

Storage module 50 can be used to store information that is used by other components of processor 26 and/or processor 14 to determine the compensation factor. For example, storage module 50 may store start times and/or end times used to determine $t_{age}$ and/or $t_{use}$, $t_{age}$ and/or $t_{use}$ themselves, a look-up table used by compensation module 48 to determine the compensation factor, a mathematical function used by compensation module 48 to determine the compensation factor, and/or other information.

In one embodiment, processor 26 enables $t_{age}$ to be determined without involving compensation module 48. In this embodiment, storage module 50 stores a time stamp of the time that luminescable medium 24 was disposed in second sensor section 18 and/or the last time that sensor 10 was calibrated. The time stamp is transmitted to processor 14, which implements the time stamp in determining $t_{age}$ and/or the compensation factor. In a similar embodiment, processor 26 stores a time stamp in storage module 50 at the start and/or end of use each time luminescable medium 24 receives electromagnetic radiation from emitter 30. These time stamps may indicate the actual times that electromagnetic radiation was received, or some approximation thereof (e.g., when the sensor sections 16 and 18 are coupled and/or uncoupled). These time stamps are then transmitted to processor 14, which uses the time stamps to determine $t_{use}$.

In one embodiment, processor 26 and transmitter/receiver 28 include an RFID transponder with associated non-volatile memory (e.g. EEPROM, etc.). For instance, the memory associated with the RFID transponder may be used to store information related to $t_{age}$ and/or $t_{use}$ in the manner discussed above with respect to storage module 50. This information may include times, time stamps, a compensation factor and/or other information related to $t_{age}$ and/or $t_{use}$. The transmitter/receiver of the RFID transponder may operate as transmitter/receiver 28 to transmit information from processor 26 and receive information for processor 26. For example, the transmitter/receiver may transmit information from and receive information to the memory associated with the RFID transponder.

In another embodiment, transmitter/receiver 28 includes an optical transmitter (e.g., via barcodes, etc.). In this embodiment, the optical transmitter may include a visible label that provides optically encoded information. The display of the visible label may be static (e.g., printed) and/or dynamic (e.g., an LCD display, a plasma display, an OLED display, etc.). The optically encoded information may include information related to $t_{age}$ and/or $t_{use}$, such as times, time stamps, a compensation factor and/or other information related to $t_{age}$ and/or $t_{use}$. In this embodiment, portions of the visible label that are static may act as storage module 50 (e.g., by storing the information) and transmitter/receiver 28 (by optically transmitting the information). In this embodiment, portions of the visible label that are dynamic may act as transmitter-receiver 28, while a processor communicatively linked to drive the dynamic display may provide some or all of the functionality of processor 26 discussed above. In this embodiment, transmitter/receiver 34 would include an optical code reader to receive information from the optical display.

Figure 5:
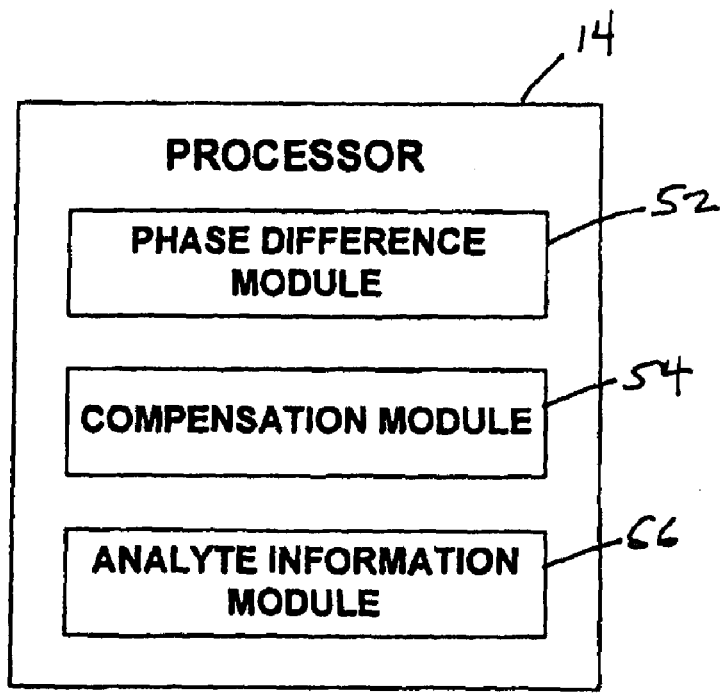
FIG. 5 illustrates a processor that determines information related to one or more analytes in a body of gas, in accordance with one embodiment of the invention.

FIG. 5 illustrates an embodiment of processor 14 including a phase difference module 52, a compensation module 54, and an analyte information module 56. Modules 52, 54, and 56 may be implemented in software; hardware; firmware; some combination of software, hardware, and/or firmware; and/or otherwise implemented. It should be appreciated that although modules 52, 54, and 56 are illustrated in FIG. 1 as being co-located within a single processing unit, processor 14 may include multiple processing units, and that some of these processing units may be located remotely from each other. In such embodiments, one or more of modules 52, 54, and 56 may be located remotely from the other modules and operative communication between the modules may be achieved via one or more communication links. Such communication links may be wireless or hard wired.

Phase difference module 52 determines a phase difference between (1) the amplitude modulation of the electromagnetic radiation from emitter 30 that becomes incident on luminescable medium 24 and (2) a modulation of electromagnetic radiation 38 luminesced by luminescable medium 24 in response to the electromagnetic radiation emitted by emitter 30.

In order to determine this phase difference, phase difference module 52 obtains the amplitude modulation of the electromagnetic radiation from emitter 30. In one embodiment, the amplitude modulation of the electromagnetic radiation from emitter 30 is obtained in the form of a periodic signal (e.g., a sinusoidal signal, a square signal, etc.) that varies in proportion to, and/or with the frequency of, the amplitude modulation of the electromagnetic radiation. This signal may be obtained from a modulated power signal that is provided to emitter 30, from a modulated power signal used to drive an active optical element that amplitude modulates the electromagnetic radiation emitted by emitter 30, or from a signal related to the positioning of passive optical elements between emitter 30 and luminescable medium 24 to amplitude modulate the electromagnetic radiation provided to luminescable medium 24.

Phase difference module 52 also obtains an amplitude modulation of electromagnetic radiation 38 that is luminesced by luminescable medium 24. In some embodiments, the amplitude modulation of electromagnetic radiation 38 that is luminesced by luminescable medium 24 is obtained in the form of a signal that varies in proportion to, and/or with the frequency of, the amplitude modulation of luminesced electromagnetic radiation 38. For example, this signal may be obtained from the one or more output signals generated by photosensitive detector 32.

Phase difference module 52 determines a phase difference between the obtained amplitude modulation of the electromagnetic radiation emitted by emitter 30 and the obtained amplitude modulation of luminesced electromagnetic radiation 38. In some instances, phase difference module 52 includes a lock-in amplifier that generates a DC signal proportional to the phase difference between these two amplitude modulations. In other instances, phase difference module 52 may be embodied in software that calculates the phase difference between the obtained amplitude modulations of the radiation emitted by emitter 30 and luminesced by luminescable medium 24.

Compensation module 54 compensates for one or more systems delays. For example, compensation module 54 compensates for the fluctuations in the response of sensor 10 caused by the deterioration of luminescable medium 24 discussed above. Compensation module 54 uses information about the deterioration of luminescable medium 24 received from processor 26 (e.g., from compensation module 48 and/or storage module 50) to compensate for these fluctuations. As was discussed above, the information about the deterioration of luminescable medium 24 received from processor 26 may include a compensation factor. The compensation factor may include a compensation to be applied to (1) the amplitude modulation of the electromagnetic radiation emitted by emitter 30, (2) the amplitude modulation of luminescent radiation 38 (as indicated by the output signals of photosensitive detector 32), and/or (3) the phase difference determined by phase difference module 52.

In some embodiments, processor 26 may provide compensation module 54 with information that is more "raw" than a determined compensation factor. For example, processor 26 may provide compensation module 54 with values for $t_{age}$ and/or $t_{use}$, or information (e.g., time stamps) from which $t_{age}$ and/or $t_{use}$ can be determined. In these instances, compensation module 54 processes the information in the manner discussed above to determine the compensation factor before making the compensation for the deterioration of luminescable medium 24.

Analyte information module 56 determines information related to one or more analytes in the body of gas within conduit 22 based on the phase difference between the amplitude modulation of the electromagnetic radiation emitted by emitter 30 that is incident on luminescable medium 24 and the modulation of electromagnetic radiation 38 that is emitted by luminescable medium 24, as determined by phase difference module 52. For example, the phase difference determined by phase difference module 52 (with compensation by compensation module 54) is related to the decay time of the luminescence of luminescable material 24.

As was mentioned above, the decay time of luminescable material 24 varies as a function of an amount of one or more gases present at luminescable medium 24. Therefore, analyte information module 56 is able to determine information related to these one or more gases (e.g., an amount present at luminescable material 24) based on the phase difference determined by phase difference module 52. For example, analyte information module 56 may determine a concentration, a partial pressure, and/or other information related to the one or more gases. In some embodiments, the one or more gases may include oxygen.

Although in the description above, compensation for the deterioration of luminescable medium 24 is described as being made by compensation module 54 prior to the determination of analyte information by analyte information module 56, alternatives to this arrangement exist. For instance, in one embodiment a compensation factor is determined (by processor 26 or compensation module 54) that adjusts the analyte information determined by analyte information module 56. In this embodiment, the compensation factor is not applied by compensation module 54 until after analyte information module 56 has determined analyte information based on uncompensated information.

The information related to $t_{age}$ and/or $t_{use}$ can also be used for other purposes within system 10. For example, information related to $t_{age}$ and/or $t_{use}$ can be used to determine when luminescable medium 24 has exceeded its useful lifetime (e.g., accurate determinations of information may no longer be made based on its luminescent properties). In this embodiment, a signal may be given to the user (e.g., a visible signal, an audible signal, etc.) that luminescable medium 24 should be replaced. Replacement of luminescable medium 24 may include replacing luminescable medium 24 within second sensor section 18 or replacing second sensor section 18 with another sensor section that includes a "younger" luminescable medium.

It should be appreciated that although the system and methods described above have been set forth in the context of analyzing gaseous analytes, the general principles of the invention are more far reaching. For instance, the principles of adjustment for system inaccuracies in sensors caused by deterioration of one or more sensor components over time may be extended to other types of detectors and/or analyzers without departing from the scope of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sensor that generates an output signal in response to a stimulus, wherein the output signal is generated with a predetermined relationship to one or more properties of the stimulus such that the one or more properties of the stimulus can be determined as a function of the output signal, the sensor comprising:
   a component that deteriorates, wherein the deterioration of the component causes predictable fluctuations in the predetermined relationship between the output signal and the one or more properties of the stimulus;
   a sensor processor that provides information related to the deterioration of the component; and
   a transmitter that wirelessly transmits the information provided by the processor,
   wherein the component deteriorates at a rate that is substantially proportional to an amount of time, and wherein the sensor processor provides information related to the amount of time, and
   wherein the amount of time includes a total amount of time that has elapsed since the sensor was last calibrated, and wherein calibrating the sensor includes determining the predetermined relationship between the output signal and the one or more properties of the stimulus that enables the one or more properties of the stimulus to be determined as a function of the output signal.

2. The sensor of claim 1, wherein the information related to the amount of time that is provided by the sensor processor includes the total amount of time that has elapsed since the sensor was last calibrated.

3. The sensor of claim 1, wherein the information related to the amount of time that is provided by the sensor processor includes a compensation factor that is determined by the sensor processor as a function of the total amount of time that has elapsed since the sensor was last calibrated.

4. The sensor of claim 1, wherein the amount of time includes an amount of time the sensor has been in use since sensor was last calibrated, and wherein calibrating the sensor includes determining the predetermined relationship between the output signal and the one or more properties of the stimulus that enables the one or more properties of the stimulus to be determined as a function of the output signal.

5. The sensor of claim 4, wherein the information related to the amount of time that is provided by the sensor processor includes the amount of time the sensor has been in use since the sensor was last calibrated.

6. The sensor of claim 4, wherein the information related to the related to the amount of time that is provided by the sensor processor includes a compensation factor that is determined by the sensor processor as a function of the time the sensor has been in use since the sensor was last calibrated.

7. The sensor of claim 1, further comprising an RFID transponder that provides the storage module and the transmitter.

8. The sensor of claim 1, further comprising:
   a receiver that receives the information transmitted by the transmitter;
   a first sensor section that carries the receiver, the first sensor section being in operative communication with a system processor such that the information received by the receiver is transferred to the system processor; and
   a second sensor section that carries the component, the sensor processor, and the transmitter, wherein the second sensor section is configured to removably couple to the first sensor section, and wherein the system processor implements the information that is transferred from the receiver to adjust a determination of information related to one or more analytes being monitored by the sensor.

9. The sensor of claim 1, further comprising a thermal capacitor for maintaining the component at a substantially constant operating temperature, wherein the thermal capacitor is located in a flow path of fluid to be detected by the sensor, wherein the stimulus enters the flow path through a window, and wherein the thermal capacitor is located over the window and the component is located over the thermal capacitor exposed to the flow path so that the stimulus passes through the thermal capacitor first and then is incident on the component.

* * * * *